United States Patent [19]

Fentress et al.

[11] Patent Number: 4,707,335

[45] Date of Patent: Nov. 17, 1987

[54] SYSTEM AND APPARATUS FOR DISINFECTING, FOR REUSE, SEPARATION DEVICES FOR BLOOD AND ASSOCIATED FLUID LINES

[75] Inventors: Philip W. Fentress, Deerfield; Rodney S. Kenley, Evanston; William J. Schnell, Libertyville, all of Ill.

[73] Assignee: Baxter Travenol Laboratories, Inc., Deerfield, Ill.

[21] Appl. No.: 769,032

[22] Filed: Aug. 26, 1985

Related U.S. Application Data

[63] Continuation of Ser. No. 524,705, Aug. 19, 1983, Pat. No. 4,552,721.

[51] Int. Cl.⁴ .......................... A61L 2/18; A61M 1/16
[52] U.S. Cl. .................................. 422/44; 210/321.3; 210/321.71; 422/292
[58] Field of Search ............... 210/927, 636, 646, 647, 210/321.3, 321.4; 422/28, 31, 44, 48, 291, 292

[56] References Cited

U.S. PATENT DOCUMENTS 4,375,413  3/1983  Geel et al. ........................... 210/636
4,431,560  2/1984  Lake et al. ....................... 134/22.19

Primary Examiner—Ivars Cintins
Attorney, Agent, or Firm—Paul C. Flattery; Daniel D. Ryan

[57] ABSTRACT

A method and a relaed apparatus for disinfecting, for reuse, separation devices for blood (10) is disclosed. Devices which may be disinfected, for reuse, include dialyzers, filters and membrane plasmapheresis devices including their interconnected and associated blood lines and intravenous administration sets. Subsequent aseptic reuse of the separation devices for blood (10) and their connected, associated blood lines and intravenous administration sets is possible.

2 Claims, 8 Drawing Figures

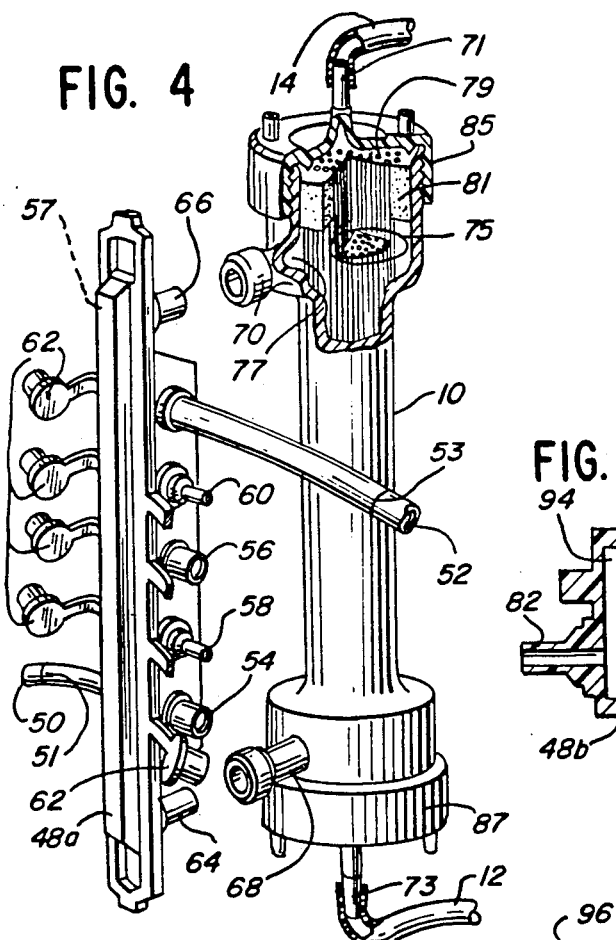
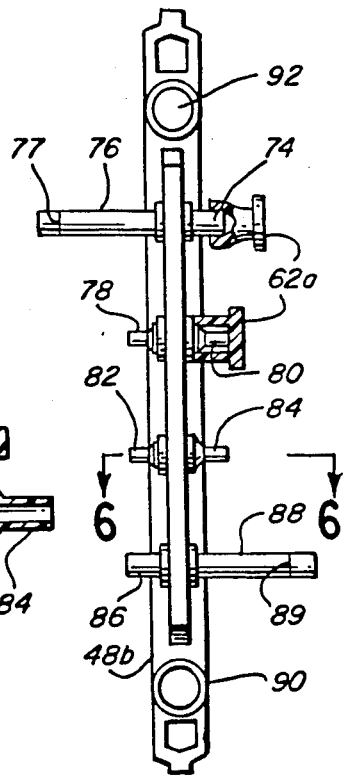
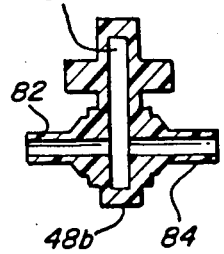
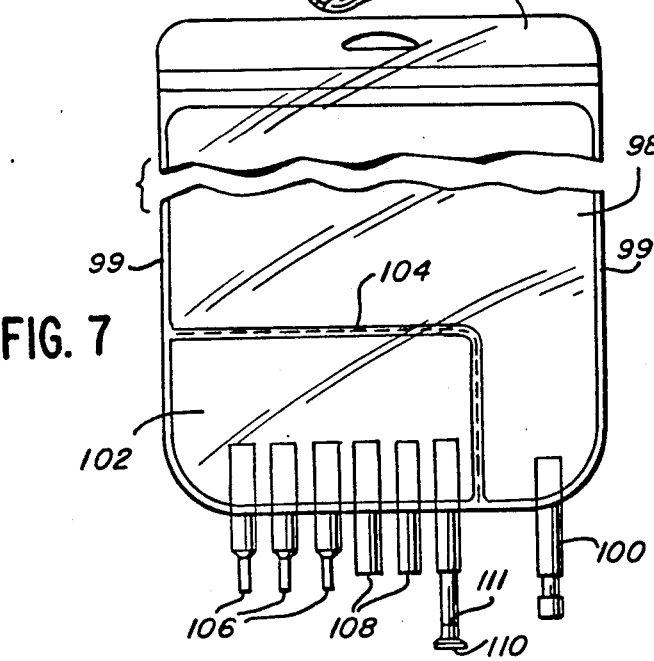
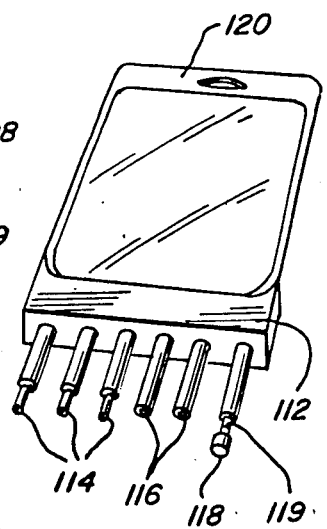

SYSTEM AND APPARATUS FOR DISINFECTING, FOR REUSE, SEPARATION DEVICES FOR BLOOD AND ASSOCIATED FLUID LINES

This application is a division of U.S. patent application Ser. No. 524,705 filed Aug. 19, 1983 now U.S. Pat. No. 4,552,721.

FIELD OF THE INVENTION

The general field of the invention pertains to methods and techniques for disinfecting or rendering antiseptic medical devices contacting blood particularly when those medical devices are used once and may be used again if properly disinfected or reprocessed. The specific province of this invention involves a method and related apparatus for disinfecting, for reuse, separation devices for blood including dialyzers, filters and membrane plasmapheresis devices and their connected, associated blood lines and intravenous administration sets. Subsequent, preferably aseptic, reuse of separation devices for blood, connected blood lines and associated intravenous administration sets is possible.

BACKGROUND OF THE INVENTION

Reuse of hemodialyzers has been increasing steadily. Reuse is motivated by economies of reuse over disposal of hemodialyzers after each use. There has been a great demand for products which disinfect, sterilize or aid in the disinfection or sterilization of hemodialyzers for their reuse. In the context of this invention, "hemodialyzer" and "dialyzer" are used synonymously.

Manufacturers have introduced automated hardware for reprocessing dialyzers for reuse. For example, Renal Systems, Inc., has introduced a machine which disinfects dialyzers for reuse. Their RENATRON TM RS-8300 is a dialyzer reprocessing system for hollow fiber dialyzers. Seratronics, Inc., as well, has introduced a machine for disinfecting dialyzers. The Seratronics' DRS-4 is a microprocessor based system designed to reprocess hollow fiber hemodialyzers for multiple use. Disadvantages associated with automated machinery are rife. Capital outlays or leasing costs for these machines are high, maintenance must be performed routinely if breakdowns are to be avoided, and when breakdowns do occur, no alternatives are provided for reprocessing the dialyzers.

Manually disinfecting dialyzers for reuse presently is the most common practice followed by reusers in hospitals and hemodialysis clinics. Typically, dialyzers are rinsed and stored with a reuse, disinfectant solution. Current reuse techniques, however, vary from place to place. Moreover, present reuse techniques for disinfecting dialyzers require disconnection and disposal of blood lines and associated intravenous administration sets.

Reuse solutions for dialyzers are available, for example, The Sporicidin Co., manufactures a solution known as SPORICIDIN ® Cold Sterilizing Solution which may be used for disinfecting and washing out dialyzers. Also, formaldehyde currently is being used for disinfecting and washing out dialyzers. U.S. patent application Ser. No. 453,080, Washing and Storage Solution for Separation Devices, to Lake, et al., [hereinafter cited as Lake] assigned to Baxter Travenol Laboratories, Inc., discloses an acidic solution for cleaning and storing blood dialyzers and other separation devices. A solution of about 1% monoperoxysuccinic acid and 8% acetic acid also may be used for cleaning and storing blood dialyzers and other separation devices, particularly intended for contact with blood after they have been used once.

It would be desirable to provide a procedure or method for disinfecting dialyzers, filters, membrane plasmapheresis devices and the like which may be quickly and uniformly performed in clinics and hospitals with minimal compromise to the sterility of the separation device. Such a method would avoid the disadvantages concomitant with specialized, automated machinery used for disinfecting dialyzers for reuse, namely, high cost, maintenance, and breakdown problems.

It would be expedient to provide a method and associated apparatus for disinfecting separation devices for blood, including dialyzers, filters, membrane plasmapheresis devices and the like, which would allow as many as possible associated blood lines and administration sets to be disinfected for reuse. The overall cost of the method and functionally related devices desirably would be less than the cost of providing a new separation device and new associated blood lines and administration sets.

It would be expedient if such a functionally related device organized the many administration set lines, blood lines and their peripheral lines. Moreover, such a device could be used with plugs for closing dialysate connectors on dialyzers to retain disinfecting reuse fluid in the dialysate compartment of the dialyzer.

It also would be desirable to neatly contain, for proper disposal, spent reuse solution not retained in the dialyzer and associated lines, by providing a receptacle for the solution.

Furthermore, it would be beneficial if connectors on the device had sealing caps to close any unused connectors thereby maintaining sterility and providing a closed system.

BRIEF SUMMARY OF THE INVENTION

The present invention is for a method of disinfecting separation devices for blood including dialyzers, filters, membrane plasmapheresis devices or the like and their interconnected, associated blood lines and intravenous administration sets, after they once have been used, particularly those lines and sets intended for contact with blood. The interconnected, associated blood lines and intravenous administration sets for use with separation devices often are referred to as a blood circuit.

By way of illustration, the method allows for the preferably aseptic reuse of dialyzers. It also allows for the preferably aseptic reuse of blood lines and intravenous administration sets used with dialyzers and heretofore disposed of after one use.

Blood inlet and outlet lines have their device ends communicating with the blood inlet and outlet on the dialyzer or other separation device. The patient end of one blood line or another of the interconnected lines for use with the separation device is connected to a container of reuse solution. Reuse solution flows from the container through the connected line and dialyzer or device and through the other connected lines.

An apparatus of the present invention is a manifold particularly adapted for use in the method. The manifold functions to provide a common connection which allows all tubing lines to be in interconnected flow relation. The manifold has an interior cavity and enough adapter-connectors accessing the cavity for connecting blood lines and intravenous administration set lines thereto. Orifices in the adapter-connectors accessing the manifold cavity act as fluid flow restrictors. The orifices are sized to account for the particular length and inside diameter of line designed to be connected thereto. By sizing the orifices, it is intended that resistance to flow be substantially equal in the lines of the blood circuit in order that each line of the blood circuit receives a substantially equal volume of reuse solution during a reuse procedure. Also, this ensures that the lines receive a substantially equal volume of saline solution during subsequent priming. A closed flow circuit for reuse solution retained in the tubing lines and device, thus, is formed.

Generally, a hemodialyzer, arterial and venous blood lines, arterial and venous needles, and an administration set are used with a dialysis control unit to administer a hemodialysis treatment. Cobe Laboratories, Inc., of Lakewood, Colorado, markets a dialysis control unit known as the CENTRY® II (CENTRY® is a registered trademark of Cobe Laboratories, Inc.) used in administering a hemodialysis treatment. Preparation for a dialysis treatment requires the blood lines, administration set and dialyzer to be primed with saline solution. After priming, the patient ends of venous and arterial blood lines are connected to the patient using fistula needle sets. Device ends of the blood lines, of course, are connected to the dialyzer.

A dialysis treatment typically lasts four to five hours. When the treatment is terminated, the arterial fistula needle is removed from the patient and injected into the injection site on a container of saline solution for rinse back of blood. Blood within the blood lines and dialyzer is rinsed back through the arterial blood line, administration set and dialyzer through the venous blood line. Once rinse back is completed, the venous blood line is clamped off. The venous needle is removed from the patient, thus terminating the hemodialysis treatment.

Principally, the method of this invention involves disinfecting a hemodialyzer and associated fluid lines. After rinse back, the patient end of typically the venous blood line is connected to a container of reuse solution. Reuse solution which may be used with the method are the 1% monoperoxysuccinic acid and 8% acetic acid solution or the reuse solution of the Lake patent application. Connection to a container of reuse solution easily can be done by injecting the venous fistula needle into an injection site on the container. Reuse solution may then flow through the venous blood line, dialyzer, arterial blood line and intravenous administration set. Flow of reuse solution preferably is from blood outlet side to blood inlet side. Flow of reuse solution alternatively may be from blood inlet side to blood outlet side, but more connections and disconnections of lines are involved. Other connection schemes are possible too. Peripheral lines, such as the venous pressure monitoring line, the arterial pressure monitoring line, the anticoagulant line, the saline administration set, and the like may be connected to the container of reuse solution and used to introduce reuse solution into the dialyzer and associated lines, rather than using the venous line for that purpose.

With a dialyzer, flow of reuse solution preferably would be from venous side to arterial side. It is believed that flow in this direction facilitates removal of protein residue, blood clots and the like—which tend to accumulate in the arterial header of the dialyzer—from the dialyzer while providing bacteriocidal effect. In addition, by directing reuse solution from the venous side to the arterial side, fewer disconnections and connections of tubing lines are required. Thus, compromises to the sterility of the system are minimized.

Compromises to the sterility of the system also are minimized by using the already attached saline solution container as a receptacle for spent reuse solution that has been rinsed through the dialyzer and lines and which is not retained therein. In addition to minimizing the compromises to sterility, the saline solution container neatly contains the spent solution until it can be disposed of properly.

The connection manifold particularly suited for use in the method allows the arterial and venous blood lines—having peripheral lines for connection to various medical devices—and the intravenous administration set to be interconnected forming a closed fluid circuit. The manifold typically has a sufficient number of female connectors, male connectors and piercable membrane tube connectors to communicate with most of the blood tubing lines currently being manufactured. For example, Medisystems Corporation, of Palo Alto, Calif., markets arterial blood tubing lines and venous blood tubing lines. Their arterial blood line typically has ancillary lines for connecting to a heparin or other anticoagulant source, a saline source and an arterial pressure monitoring device. The venous blood tubing line marketed by Medisystems Corporation typically has an ancillary venous pressure monitoring line. These lines are connected to the manifold during the reuse method.

The manifold also may have a piercable membrane tube to accommodate the spike end of a saline administration set. The other end of the saline intravenous administration set generally is connected to the arterial blood line.

Orifices in the connectors accessing the manifold cavity act as fluid flow restrictors. The orifices are sized to account for the particular length and inside diameter of line designed to be connected thereto. By appropriately sizing the orifices, resistance to flow is substantially equalized in the blood lines and other interconnected lines in order that each line receives a substantially equal volume of reuse solution during a reuse procedure. Also, this ensures that the lines receive a substantially equal volume of saline solution during subsequent priming.

Another apparatus used in the present invention comprises the dialyzer or other separation device defining a blood flow path and a second flow path separated from the blood flow path by semi-permeable membrane means. A blood inlet and a blood outlet access the blood flow path, and port means access the second flow path. The device end of the blood inlet line communicates with the blood inlet on the device. The device end of the blood outlet line communicates with the blood outlet on the device. A manifold defining an open interior cavity and an exterior having connectors which communicate with the patient ends of the blood inlet and outlet lines forming a common connection which allows the blood lines to be in interconnected flow relation through their patient ends. Disinfecting reuse solution is carried within the separation device, the blood lines and the manifold cavity.

The blood lines of this apparatus may have peripheral lines, for example, pressure monitoring lines on both blood inlet and outlet lines, an anticoagulant line on the blood inlet line, and possibly a protamine infusion line on the blood outlet line. A saline intravenous administration set, used in priming the separation device and associated lines before use and in rinsing back blood after use, also may communicate with the blood inlet line.

The method of this invention also may be used for disinfecting membrane plasmapheresis devices and their associated fluid lines. After rinse back of the blood lines and the membrane plasmapheresis device has been completed, the blood outlet line—communicating at its device end with the blood outlet of the device—may be connected at its patient end to a container of reuse solution. Reuse solution then may flow through the blood outlet line, membrane plasmapheresis device, blood inlet line and any intravenous administration set. Flow of reuse solution preferably would be in a direction from the blood outlet side to the blood inlet side of the membrane plasmapheresis device, that is, in a direction opposite conventional blood flow. It is believed that flow of reuse solution in this direction facilitates removal of protein residue, blood clots and the like— which tend to form and accumulate in the inlet header of the device—from the device while providing bactericidal effect. Also, by directing reuse solution in this way, fewer disconnections and connections of blood lines and intravenous lines would be necessary. Compromises to sterility within the system would be minimized. Spent reuse solution that has been rinsed through the device and lines and not retained therein can be disposed of properly by using the already connected, empty saline solution container as a receptacle therefor.

The connection manifold also may be used with a membrane plasmapheresis device for performing the reuse method. The blood lines, having peripheral lines for connection to various medical devices, and the intravenous administration set could be interconnected using the manifold to form a closed fluid circuit.

A manifold, having a sufficient number of female connectors, male connectors and piercable membrane tube connectors to communicate with the tubing lines desirably would be used in a membrane plasmapheresis reuse procedure. Orifices in the connectors accessing the manifold cavity would act as fluid flow restrictors. The orifices would be sized to account for the particular length and inside diameter of line designed to be connected thereto. Resistance to flow would be substantially equalized in order that the interconnected lines would receive substantially equal volumes of reuse solution during a reuse procedure.

One benefit of this invention is the ability to disinfect a dialyzer without the use of specialized automated machinery. Initial capital outlay, maintenance and breakdown problems associated with automated machinery therefore are avoided.

An additional benefit of the method is its elegance. This procedure may be performed quickly, easily and uniformly with minimal compromise to the sterility of the blood lines, dialyzer or administration set.

Another benefit of a preferred embodiment of this invention is that spent reuse solution that has been rinsed through the separation device and not retained therein may be disposed of properly by using an already connected, substantially empty saline solution container as a receptacle therefor.

The method also is useful in disinfecting other separation devices for blood including filters and membrane plasmapheresis devices and their associated blood and fluid lines. The method may be performed quickly with these devices, with minimal compromise to the sterility of the devices and blood and fluid lines.

Heretofore unobserved benefits of this method are the ability to prepare, for reuse, blood lines, fluid lines and other devices previously discarded after a single use. Blood lines and administration lines may be disinfected while still connected to the dialyzer, membrane plasmapheresis device or filter. Further reductions in the cost of separation treatments for blood thus may be realized.

An advantage of introducing the reuse solution through the venous line (or blood return line of a membrane plasmapheresis device) is the facilitation of the washing away of protein-containing residues, for example, blood clots and fibrin.

An added benefit of the method as practiced with dialyzers inheres in the use of a dialysis control unit for pumping reuse solution from the reuse solution container. Reuse solution preferably can be pumped through the dialyzer and its associated blood and fluid lines merely by reversing the arterial blood line pump segment in the blood pump of a control unit.

Other benefits and advantages of this invention will become apparent upon reading the following detailed description and appended claims.

BRIEF DESCRIPTION OF THE DRAWINGS

For a more complete understanding of this invention, reference should now be had to the embodiments illustrated in greater detail in the accompanying drawings.

In the drawings:

FIG. 4 is a perspective view of the manifold of this invention, particularly suited for use in the method, showing connectors with caps, piercable membrane ports and plugs for the dialysate connectors on the dialyzer.

FIG. 5 is a plan view of a preferred embodiment of the manifold showing male, female and piercable membrane connectors.

FIG. 6 is a cross-section taken at 6—6 of FIG. 5 showing the manifold interior cavity.

FIG. 7 is a plan view of another embodiment of the manifold of the present invention formed with, and separable from, a reuse solution container bag.

FIG. 8 is a perspective view of another embodiment of the manifold of this invention.

DESCRIPTION OF THE PREFERRED EMBODIMENTS

Figure 1:
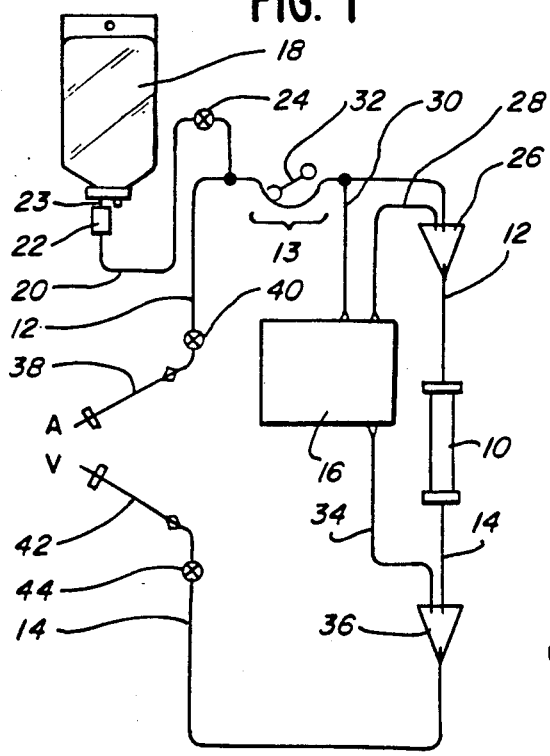
FIG. 1 is a schematic diagram showing the basic components used in administering a hemodialysis treatment in accordance with current technology.

A general schematic representation of a dialysis control unit with devices used in a dialysis treatment is illustrated in FIG. 1. Dialyzer 10 is shown connected to the device end of arterial or inlet blood line 12 and the device end of venous or outlet blood line 14. Blood inlet 71 and blood outlet 73 are shown on dialyzer 10 in FIG. 4. The device end of arterial or inlet blood line 12 is connected to blood inlet 71, and the device end of venous or outlet blood line 14 is connected to blood outlet 73. Also shown in FIG. 1 are dialysis control unit 16 with its associated blood pump 32 and saline solution container 18.

Prior to a hemodialysis treatment, blood inlet line 12, blood outlet line 14 and dialyzer 10 are primed with saline solution from container 18. Administration set 20 connects saline container 18 and arterial blood line 12. Administration set 20 has bubble trap 22 and clamp 24 thereon. Generally, bubble trap 22 terminates in a spike which is used to pierce piercable membrane tube 23 on saline container 18. Clamp 24 is typically a roller clamp, and administration set 20 typically terminates at its other end in a male Luer connector for connection to arterial blood line 12.

Bubble trap 26, in arterial line 12, is upstream of dialyzer 10. Arterial pressure line 28, connected to bubble trap 26, also connects to dialysis control unit 16 for monitoring arterial pressure. Anticoagulant infusion line 30 administers heparin or other suitable anticoagulant from the dialysis control unit 16 to arterial line 12. Also, blood pump portion 13 of arterial line 12 is placed in blood pump 32. Venous pressure monitoring line 34 connects venous bubble trap 36 downstream of dialyzer 10 and dialyzer control unit 16.

Arterial blood line 12 typically terminates at its patient end in a male Luer connector which connects to the female Luer connector of arterial fistula tube and needle set 38. Clamp 40 is provided near the patient end of arterial blood line 12 for controlling blood flow through the line. Venous blood line 14 terminates at its patient end in a male connector which connects to a female connector of venous fistula tube and needle set 42. Clamp 44 is provided near the patient end of venous blood line 14 for control of blood flow therethrough.

After a dialysis treatment, blood is typically rinsed from arterial or inlet line 12 through dialyzer 10 and back into the patient at outlet or venous line 14. Saline solution from saline container 18 is used to perform this rinse back procedure. In performing the rinse back procedure, arterial fistula needle set 38 is removed from the patient and injected into an injection site on saline container 18. Saline solution flows from container 18 through arterial fistula needle set 38, arterial line 38 and administration set 20 through dialyzer 10 to venous line 14. After rinse back has been completed, fistula needle set 38 and saline administration set 20 remain connected to saline solution container 18. Clamps 24, 40 and 44 are closed, and needle 42 is withdrawn from the patient.

Figure 2:
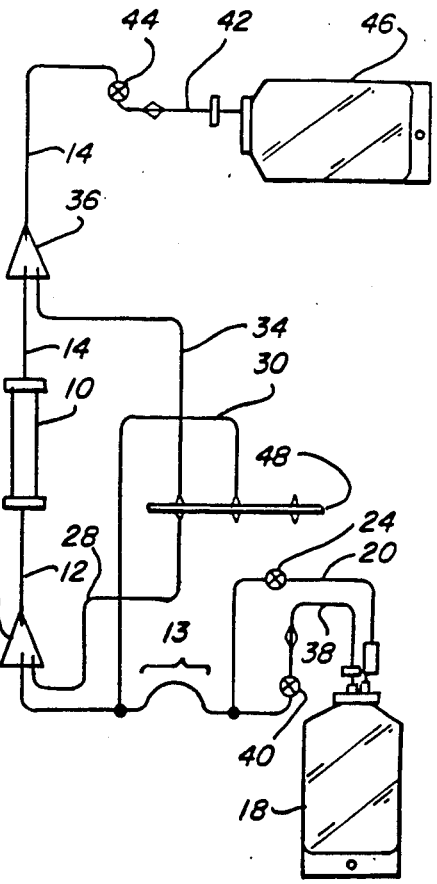
FIG. 2 is a schematic diagram which portrays the administration of reuse solution to the blood lines, dialyzer and administration set used in a hemodialysis treatment.

The reuse method of the present invention is illustrated in FIG. 2. With fistula needle set 38 and saline administration set 20 still connected to saline container bag 18, venous fistula needle set 42 is connected to reuse solution container 46. The medical device end of venous pressure line 34, arterial pressure line 28 and heparin line 30 are connected to manifold 48 of the present invention. Manifold 48 provides a common connection which allows all tubing lines to be in interconnected flow relation through a cavity in manifold 48, which also provides a repository for reuse solution. Manifold 48 serves to keep closed the system of blood lines, administration sets and dialyzer. Blood pump portion 13 of arterial blood line 12 is removed from blood pump 32, and clamps 24, 40 and 44 are opened to allow reuse solution from container 46 to flow through the circuit.

Reuse solution flows through venous or outlet line 14 to bubble trap 36. The reuse solution of the Lake patent application may be used. Reuse solution flows through venous pressure line 34 to the manifold 48 and through dialyzer 10. Reuse solution, which migrates across the membrane of the capillary fibers of the dialyzer to the dialysate side, is prevented from exiting the dialyzer by closing or plugging the dialysate ports 68, 70 (FIG. 4) on dialyzer 10. Reuse solution flow is preferred from venous or outlet header 87 to arterial or inlet header 85 because protein residue, blood clots, fibrin and the like tend to accumulate at the arterial or inlet header 85 during use of the dialyzer 10.

Reuse solution proceeds through arterial or inlet line 12 and bubble trap 26. Reuse solution fills arterial pressure line 28 and heparin line 30. Reuse solution, carrying blood residue and the like, then flows into saline container 18 through saline administration line 20 and arterial fistula set 38, which may be lowered below the rest of the set for gravity flow.

A quantity of reuse solution sufficient to rinse the dialyzer and associated blood lines and sets flows through the system. A volume of reuse solution is left in the dialyzer, lines and sets, typically enough essentially to fill the system. Clamps 24, 40 and 44 are closed to prevent further fluid flow. Arterial and venous needle fistula sets 38, 42 are then detached from the arterial or inlet line 12 and the venous or outlet line 14. The patient ends of arterial and venous lines are connected to manifold 48. Saline intravenous administration line 20 is unspiked from saline container 18 and injected into a piercable membrane tube site on manifold 48. The reuse solution washed into saline container 18 and container 18 are discarded.

Figure 3:
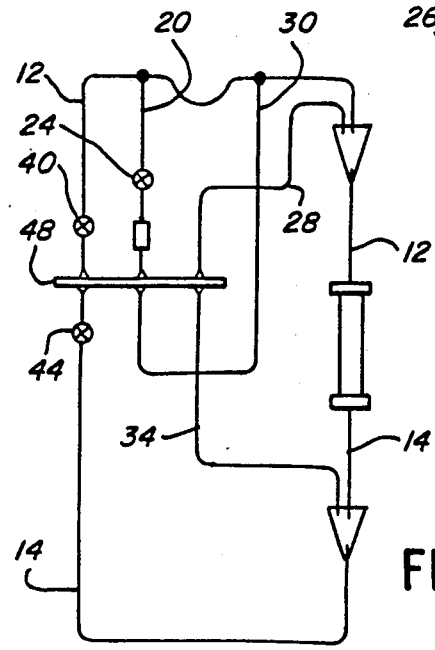
FIG. 3 is a schematic diagram showing the blood lines, having peripheral lines, and an administration set interconnected at the manifold of the invention to form a closed circuit.

FIG. 3 illustrates, schematically, blood lines 12 and 14 with their associated pressure lines 28 and 34, saline line 20, and heparin line 30 connected to manifold 48. A closed circuit is thus formed, and the reuse solution is retained within the circuit. Clamps 24, 40 and 44 may be opened to allow free flow of reuse solution throughout the circuit. Dialysate ports in dialyzer 10 preferably are closed or plugged. The dialyzer and associated lines and sets then may be stored, with reuse solution therein, until their next use in a dialysis treatment.

The reuse method of the present invention also may be practiced on a membrane plasmapheresis device and its associated blood inlet and outlet lines and intravenous administration set. The device ends of the blood inlet and outlet lines would be connected to the membrane plasmapheresis device. The patient ends of the blood inlet and outlet lines would be connected to needle sets.

In a manner similar to the rinsing and disinfecting of a dialyzer, reuse solution would flow from the patient end of the blood outlet line to the membrane plasmapheresis device and then through the blood inlet line. Any open connectors on the membrane plasmapheresis device would be closed or plugged. Reuse solution would fill any peripheral pressure lines, anticoagulant infusion lines, or the like. A saline solution container communicating with the blood inlet line would accommodate spent reuse solution not retained in the blood lines or the plasmapheresis device.

Once rinsing with reuse solution is completed, the patient ends of the blood inlet and outlet lines, and any other associated lines would be connected to the manifold of the present invention forming a closed circuit. The membrane plasmapheresis device and its associated lines and sets then may be stored, with reuse solution therein, until the next use of the device.

Alternatively, a separation device for blood, for example dialyzer 10, may be washed with reuse solution by introducing reuse solution at the patient end of arterial line 12, at the bubble trap end of saline administration set 20, at the medical device end of anticoagulant infusion line 30, at the medical device end of arterial pressure monitoring line 28, at the medical device end of venous pressure monitoring line 34 or the like. The separation device for blood and its associated lines and sets thereafter may be appropriately rinsed and disinfected with reuse solution.

An embodiment of a manifold 48 finding particular utility in this invention is illustrated in FIG. 4. Manifold 48a is generally of an elongated configuration having a hollow interior. Piercable membrane tubes or ports 50, 52, carrying membranes 51 and 53 across their bores, are shown connected to manifold 48a. Female connectors 54, 56 and male connectors 58, 60 are also shown accessing the interior cavity 57 of manifold 48a. Additional male and female connectors may reside on the same side of manifold 48a as membrane port 50.

Cavity 57 interconnects all connectors and ports 50, 52, 54, 56, 58 and 60 and others not shown. These connectors and ports may be used for connecting different portions of the arterial or inlet blood line 12 and venous or outlet blood line 14 to the manifold. The spike end of the saline administration line 20 may be spiked into one of the piercable membrane ports 50, 52. The patient end of arterial or inlet blood line 12 terminating in a male connector may communicate with female connector 54 on manifold 48a. Arterial pressure line 28 terminating in a female connector may communicate with male connector 58, and heparin line 30 terminating in a female connector may communicate with male connector 60 on manifold 48a. The patient end of venous or outlet blood line 14 terminating in a male connector may communicate with female connector 56, and venous pressure line 34 terminating in a female connector may communicate with an additional male connector on manifold 48a.

Connectors and ports 50, 52, 54, 56, 58 and 60 and the others not shown have their orifices restricted or sized to selectively restrict fluid flow into cavity 57. The orifices are sized to account for the particular length and inside diameter of lines designed to be connected thereto. By sizing the orifices, it is intended that resistance to flow be substantially equal in all of the lines so that all of the lines receive a substantially equal volume of reuse solution during a reuse procedure and a substantially equal volume of saline solution during subsequent priming. This prevents fluid from shunting through preferential lines and thus bypassing other lines.

Depending on line length and inside diameter, the ports and connectors can have orifices sized to substantially equilibrate fluid flow in the lines in order that the lines receive substantially equal volumes of reuse solution during a reuse procedure or saline solution during subsequent priming.

Protective caps 62, hinged from manifold 48a, may be used to cover and seal the male and female connectors which are not in use. Plugs 64, 66 are also carried by manifold 48a. Plugs 64, 66 are sufficiently spaced for plugging into dialysate ports 68, 70 on dialyzer 10 to close them in the storage position of FIG. 3.

The various tubing lines thus may be arranged in any orderly manner on manifold 48a. The manifold typically will have a sufficient number of male and female connectors and membrane ports to accommodate the different lines used with dialyzers. Whatever the arrangement of connectors and ports, the manifold will provide a common connection which allows all tubing lines to be in interconnected flow relation. Unused connectors typically will be covered and sealed by protective caps.

Dialyzer 10, of conventional design, has blood inlet 71 in blood inlet header 85 and blood outlet 73 in blood outlet header 87. A blood flow path is defined by semipermeable membrane hollow fibers of bundle 75. A second flow path 77 is separated from open ends 79 of hollow fibers 75 by sealant 81. Both ends of dialyzer 10 are sealed in this manner, thus providing a separate fluid flow path for blood and dialysate. Dialysate ports 68, 70 access the second, dialysate flow path.

Arterial or inlet blood line 12 has its device end communicating with blood inlet 71, and venous blood line 14 has its device end communicating with blood outlet 73 on dialyzer 10. Manifold 48 provides connectors, as previously discussed, for connecting the patient ends of arterial line 12 and venous line 14 to manifold 48 forming a common connection which allows blood lines 12 and 14 to be in interconnected flow relation through their patient ends. Connectors are also provided on manifold 48 allowing peripheral lines including venous pressure line 34, arterial pressure line 28, anticoagulant or heparin line 30 and saline intravenous administration set 20 to connect with and be in interconnected flow relation with the patient ends of arterial line 12 and venous line 14.

Disinfecting reuse solution, is carried within dialyzer 10, blood lines 12, 14, venous pressure line 34, arterial pressure line 28, heparin line 30, saline intravenous administration set 20 and interior cavity 57 of the manifold.

FIG. 5 illustrates another preferred embodiment of a manifold 48 of the present invention. Two rows of four connectors communicate with the interior cavity 94 of the manifold 48b. Various connectors are on opposite sides of manifold 48b. A manifold of the construction of manifold 48b may be made from two identical parts.

Manifold 48b has female connector 74 paired with piercable membrane tube 76 (carrying membrane 77 across its bore), both communicating with the interior cavity 94 of manifold 48b. Male connector pair 78, 80 and pair 82, 84 are also in opposing relationship. Female connector 86 and piercable membrane tube 88 (carrying membrane 89 across its bore) are also paired. Plugs 90, 92 are carried on manifold 48b and may be placed sufficiently apart to plug dialysate ports 68, 70 on dialyzer 10.

The patient end of arterial or inlet blood line 12 terminating in a male connector may communicate with female connector 74 on manifold 48b. Arterial pressure line 28 terminating in a female connector may communicate with male connector 80, and heparin line 30 terminating in a female connector may communicate with male connector 78 on manifold 48b. The patient end of venous or outlet blood line 14 terminating in a male connector may communicate with female connector 86, and venous pressure line 34 terminating in a female connector may communicate with male connector 82 on manifold 48b. Saline line 20 terminating with a spike end may be spiked into piercable membrane tube or port 88. For presently used blood lines and associated peripheral lines used in hemodialysis, the following orifice sizes on manifold 48b substantially equalize flow resistance through the connected lines. When arterial or inlet blood line 12 connects to connector 74, the orifice in connector 74 has an inside diameter of about 0.02 to 0.04 inch and preferably an inside diameter of 0.03 inch. Connector 80 has an orifice inside diameter of similar size, that is, about 0.02 inch to 0.04 inch and preferably an inside diameter of 0.03 inch when arterial pressure line 28 connects to connector 80. When heparin line 30 communicates with connector 78, the orifice inside diameter of connector 78 is about 0.08 inch to 0.16 inch and preferably 0.12 inch. When venous or outlet blood line 14 communicates with connector 86, connector 86 has an orifice with inside diameter of about 0.08 to 0.16 inch and preferably 0.12 inch. Also, when venous pressure line 34 connects to connector 82, connector 82 has an orifice inside diameter of about 0.02 to 0.04 inch and preferably 0.03 inch. Orifices sized accordingly in the above connectors and connected to the referenced lines will substantially equalize flow resistance in the lines connected to manifold 48b. This is intended to insure that the lines receive substantially equal volumes of reuse solution during a reuse procedure.

Protective caps 62a may be hinged and carried on manifold 48b in a manner similar to caps 62 on manifold 48a. Manifold 48b provides a common connection which allows all tubing lines to be in interconnected flow relation. Unused connectors typically will be covered and sealed by protective caps 62a.

After a reuse rinse, the quantity of reuse solution remaining in the separation device, lines and sets is typically enough to fill the system. Manifold 48b provides a repository (cavity 94) for reuse solution. FIG. 6 illustrates a sectional view of the manifold of FIG. 5 taken at 6—6. Manifold 48b has an open interior cavity 94 which allows fluid to flow in the manifold thus interconnecting all the connectors of the manifold.

FIG. 7 illustrates still another embodiment for a manifold of the present invention, made of a pair of plastic sheets heat sealed along periphery 99 and sealed line of tearing weakness 104. Reuse solution container 96 may be manufactured in compartments. First compartment 98, accessible by injection site port 100, contains reuse solution. Second compartment 102 is separated from first compartment 98 by a sealed line of weakness 104. This allows the second compartment 102 to be torn away from first compartment 98. Compartment 102 may thereafter be used as a manifold similar to manifold 48 in the method of the present invention. Compartment 102 is shown accessed by male connectors 106, female connectors 108 and piercable membrane tube or port 110 carrying piercable membrane 111 across its bore. The ports and connectors may be used for connecting different portions of the arterial or inlet blood line 12, venous or outlet blood line 14 and the saline line 20 to manifold compartment 102, similar to manifold 48.

FIG. 8 illustrates still another embodiment of the manifold of the present invention. Molded plastic piece 112, having male connectors 114, female connectors 116 and piercable membrane tube 118, carrying piercable membrane 119 across its bore, may form the bottom end of flexible container bag 120. The connectors provide access to the hollow interior of bag 120 allowing fluid to flow freely from connector to connector. The ports and connectors may be used for connecting different portions of the arterial or inlet blood line 12, venous or outlet blood line 14, and saline line 20 to manifold bag 120 similar to manifold 48.

The above has been offered for illustrative purposes, and is not intended to limit the invention of this application, which is defined in the claims below.

What is claimed is:

1. A disinfecting system which comprises:
   a separation device for blood defining a blood flow path and a second flow path separated from the blood flow path by semi-permeable membrane means, said device having a blood inlet and a blood outlet accessing the blood flow path and port means for accessing the second flow path;
   a blood inlet line having a device end and a patient end, the device end communicating with the blood inlet on said device;
   a blood outlet line having a device end and a patient end, the device end communicating with the blood outlet on said device;
   a manifold defining an interior cavity and an exterior having at least two connectors which communicate with the patient ends of said blood inlet line and said blood outlet line forming a common connection which allows said blood lines to be in interconnected flow relation through their patient ends, wherein said connectors on said manifold have orifices sized to substantially equilibrate resistance to fluid flow through lines intended to be connected thereto whereby each line receives a substantially equal volume of fluid flowing therethrough; and,
   disinfecting reuse solution carried within said separation device for blood, said blodd inlet line, said blood outlet line and said interior cavity of said manifold.

2. A disinfecting system for use with a separation device for blood defining a blood flow path and a second flow path separated from the blood flow path by a semi-permeable membrane means, the device having a blood inlet and a blood outlet accessing the blood flow path and port means for accessing the second flow path, said system comprising:
   a blood inlet line having a device end and a patient end, said inlet device end communicating with the blood inlet on the device;
   a blood outlet line having a device end and a patient end, said outlet device end communicating with the blood outlet on the device;
   a manifold defining an interior cavity and an exterior having at least two connectors which sealingly communicate with the patient ends of said blood inlet line and said blood outlet line forming a common connection with said blood lines and said manifold, wherein said connectors on said manifold have orifices sized to substantially equilibrate resistance to fluid flow through lines intended to be connected thereto whereby each line receives a substantially equal volume of fluid flowing therethrough, and
   the separation device being in fluid flow communication with disinfecting reuse solution carried within the separation device, said blood inlet line, said blood outlet line and said interior cavity of said manifold.

* * * * *